United States Patent [19]

Salari et al.

[11] Patent Number: 5,369,097

[45] Date of Patent: Nov. 29, 1994

[54] PHOSPHONATES AS ANTI-CANCER AGENTS

[75] Inventors: Hassan Salari, Ladner, Canada; Robert Bittman, Roslyn Heights, N.Y.

[73] Assignee: The University of British Columbia, Vancouver, Canada

[21] Appl. No.: 59,170

[22] Filed: May 4, 1993

Related U.S. Application Data

[63] Continuation-in-part of Ser. No. 835,732, Feb. 11, 1992, Pat. No. 5,219,845, which is a continuation-in-part of Ser. No. 692,452, Apr. 25, 1991, abandoned.

[51] Int. Cl.$^5$ ............................................. A61K 31/685
[52] U.S. Cl. .................................. 514/77; 514/114; 558/169
[58] Field of Search ................................ 514/77, 114

[56] References Cited

U.S. PATENT DOCUMENTS

| 4,408,052 | 10/1983 | Hozumi et al. | 546/22 |
| 4,515,722 | 5/1985 | Yang et al. | 554/79 |
| 5,219,845 | 6/1993 | Salari et al. | 514/77 |

FOREIGN PATENT DOCUMENTS

| 1240534 | 1/1989 | Canada . |
| 0108565 | 5/1984 | European Pat. Off. . |
| 0230575 | 4/1986 | European Pat. Off. . |
| 0338407 | 10/1989 | European Pat. Off. . |
| 0092190 | 10/1993 | European Pat. Off. . |
| 60-69088 | 4/1985 | Japan . |

OTHER PUBLICATIONS

Carter, S. K. et al., *Chemotherapy of Cancer;* Second Edition; John Wiley and Sons: New York, 1981; Appendix C.
*Chemical Abstracts*, vol. 117 (1992), p. 794, Abstract No. 90393s; Ries, U. J. et al., "Synthesis of Alkylphosphonates, a New Class of Antineoplastic Agents," *Chem. Phys. Lipids*, vol. 61, No. 3 (1992), pp. 225–234.
*Chemical Abstracts*, vol. 103, No. 21 (1985), p. 701, Abstract No. 178451f; Japan Kokai Tokyo Koho 60–069088.
*Chemical Abstracts*, vol. 114, 1991, p. 767, Abstract No. 82129h; German Democratic Rep. 278,800.
Yuan, W. et al., "Phosphate-Containing Phospholipid Analogues as Tight-Binding Inhibitors of Phospholipase-A$_2$," *J. Am. Chem. Soc.*, vol. 110 (1988), pp. 2665–2666.

*Primary Examiner*—Mary C. Lee
*Assistant Examiner*—M. G. Ambrose
*Attorney, Agent, or Firm*—Oyen Wiggs Green & Mutala

[57] ABSTRACT

This invention pertains to the synthesis and use as therapeutic agents of a group of substances with a glycerol backbone or aliphatic chain structure linked to a phosphorus atom and a polar head group. Depending on the polar head group, the substance has anti-cancer, anti-inflammatory, anti-allergy or anti-cardiovascular disease properties. Compounds of the formula:

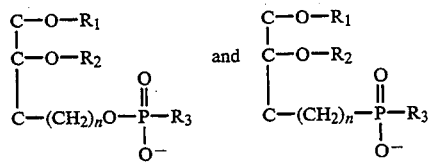

wherein n is 0 to 14 and $R_1$ is an alkyl group of $C_{12}$–$C_{20}$, $R_2$ is a methyl group, and wherein $R_3$ is an inositol analog head group, a $(CH_2)_m N^+(CH_3)_3$ group with m=2 to 10, a serine head group, or an ethanolamine head group, or of the formula

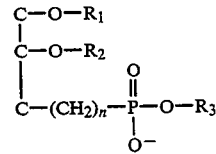

wherein $R_1$ and $R_2$ are as described above, n=0 or 1, and $R_3$ is $(CH_2)_m N^+(CH_3)_3$ (m=2–10) are claimed. This invention also pertains to the synthesis and use as (Abstract continued on next page.)

therapeutic agents of a group of substances that have no glycerol backbone but have an aliphatic chain structure linked directly to a phosphorus atom of the general formula R—P(O)(O—)OR' wherein R is a long-chain alkyl group such as hexadecyl or octadecyl and R' is a head group such as choline, glycerol, inositol, ethanolamine, or serine.

4 Claims, No Drawings

PHOSPHONATES AS ANTI-CANCER AGENTS

This application is a continuation-in-part of application Ser. No. 07/835,732, filed Feb. 11, 1992, now U.S. Pat. No. 5,219,845, which is a continuation-in-part of application Ser. No. 07/692,452, filed Apr. 25, 1991, abandoned.

FIELD OF THE INVENTION

This invention pertains to the synthesis and use as therapeutic agents of a group of substances with a glycerol backbone or aliphatic chain structure linked to phosphonocholine, phosphinocholine, phosphonoinositol, phosphinoinositol, or other phosphorus-containing head groups. Depending on the polar head group, the substance has anti-cancer, anti-inflammatory, anti-allergy, or anti-cardiovascular disease properties.

BACKGROUND OF THE INVENTION

European Patent No. P 0230 575A2, dated Apr. 12, 1986, discloses a group of glycerophospholipids compounds having an alkyl chain of C2–C22 and a methoxy group at the sn-2 position and a phosphocholine at the sn-3 position. These compounds are stated to be useful as anti-cancer agents.

U.S. Pat. No. 4,408,052, dated Feb. 25, 1981, assigned to Takeda Chemical Industries, Osaka, Japan, claims a group of phospholipid carbamates as useful as antitumor agents. Canadian Pat. No. 1,248,534, dated Jan. 10, 1989, granted to Takeda Chemical Industries of Japan, protects a group of ketolyso phospholipids, which purportedly are useful as antitumor agents.

U.S. Pat. No. 4,515,722, dated May 7, 1985, granted to Merck Sharp & Dohme, protects a group of phosphatidylinositol analogs which are evidently effective in inhibiting phospholipase C and thereby have utility as anti-inflammatory and analgestic agents.

None of these patents discloses a substance with a glycerol backbone linked to a phosphorus atom with a polar head group used as an anti-cancer, anti-inflammatory, anti-allergy, or anti-cardiovascular disease treating agents.

SUMMARY OF THE INVENTION

The present invention provides anti-leukemic phospholipids of the general formula:

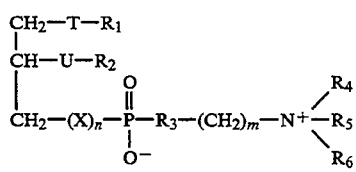

wherein T is an oxygen atom, U is an oxygen atom, or NH, $R_1$ is an aliphatic chain such as hexadecyl or octadecyl, $R_2$ is a methyl group when U is oxygen or when U is NH, X is a methylene group, n is 0 to 4, $R_3$ is either an oxygen atom or a methylene group, m is 2, 3, 4, 5, 6, 7, 8, or 9, and $R_4$, $R_5$ and $R_6$ represent alkyl groups containing 1 to 3 carbon atoms.

A compound of the formula:

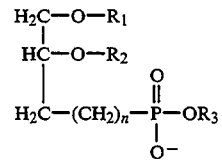

wherein n is 0 to 14 and $R_1$ is an alkyl group of $C_{12}$–$C_{20}$; wherein $R_2$ is a methyl group; and wherein $R_3$ is an inositol analog head group, a $(CH_2)_m N^+(CH_3)_3$ group with m=2 to 10, a serine head group, or an ethanolamine head group.

A phosphonate compound of the formula:

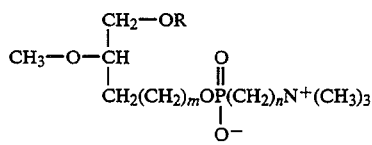

wherein R is an alkyl group such as hexadecyl or octadecyl, m=0 or 1, n=2–10, or the enantiomer thereof, or a mixture of stereoisomers.

Phosphonolipids of the general formula R—P(O)(O-)OR' wherein R is an alkyl group such as hexadecyl or octadecyl and R' is a head group such as choline, glycerol, inositol, ethanolamine, or serine.

Phosphinates of the general formula:

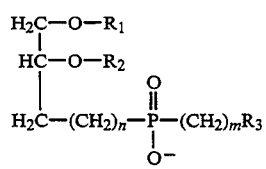

wherein n=0 or 1, $R_1$ and $R_2$ are as defined in claim 1, and $R_3$ is an inositol or $N^+(R_4)_3$ group and m=2–10, and $R_4$ is an alkyl group such as methyl, ethyl, n-propyl, or isopropyl.

The phosphonate or phosphinate compounds as claimed in described include either of the opposite stereochemical configurations [(R) or (S)], or a mixture thereof.

A phosphinate for treatment of leukemic cells having the formula:

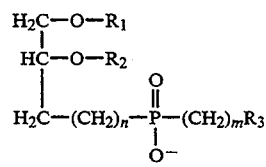

wherein $R_1$ is a long-chain alkyl group, $R_2$ is a methyl group, n=0 or 1, m=2 or 3, and $R_3$ is $N^+(CH_3)_3$, and pharmaceutically acceptable salts thereof, administered at a dosage of about 5 to 50 mg/l, with or without a carrier.

The compound as identified in the second paragraph of this summary can be used as an agent in inhibiting cancer cell growth when the compound is administered at a concentration in the range of 5 mg/l to 50 mg/l, and pharmaceutically acceptable acid or salts thereof and a pharmaceutically acceptable carrier.

The compound when used in the treatment of an inflammatory disease is administered at 5-50 mg/l in a pharmaceutically acceptable carrier.

The phosphonates or phosphinates as identified in the second, third, fourth, fifth, and sixth paragraphs of this summary can be used in the treatment of allergic skin rashes, hayfever, and asthma or cardiovascular disease when administered to the patient at a dosage of about 5-50 mg/l in association with a pharmaceutically acceptable carrier.

A method of treating cancer, inflammation, allergy or cardiovascular disease in a mammal comprising treating the mammal with a therapeutic amount of a compound of the formula:

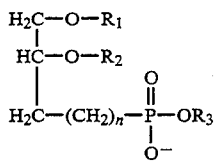

wherein n is 0 to 14 and $R_1$ is an alkyl group of $C_{12}-C_{20}$; wherein $R_2$ is a methyl group; and wherein $R_3$ is an inositol analog head group, a $(CH_2)_m N^+(CH_3)_3$ group with m=2 to 10, a serine head group, or an ethanolamine head group.

A method of treating cancer, inflammation, allergy or cardiovascular disease in a mammal comprising treating the mammal with a therapeutic amount of a compound of the formula:

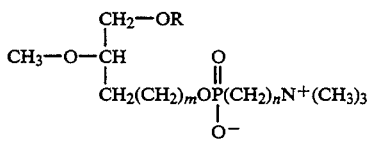

wherein R is an alkyl group such as hexadecyl or octadecyl, m=0 or 1, n=2-10, or the enantiomer thereof, or a mixture of stereoisomers.

A method of treating cancer, inflammation, allergy or cardiovascular disease in a mammal comprising treating the mammal with a therapeutic amount of a phosphonolipid of the general formula: $R-P(O)(O-)(OR')$, wherein R is an alkyl group such as hexadecyl or octadecyl and R' is a head group such as choline, glycerol, inositol, ethanolamine, or serine.

A method of treating cancer, inflammation, allergy or cardiovascular disease in a mammal comprising treating the mammal with a therapeutic amount of a phosphinate of the general formula:

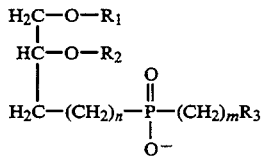

wherein n=0 or 1, $R_1$ and $R_2$ are as defined in claim 1, and $R_3$ is an inositol or $N^+(R_4)_3$ group and m=2-10, and $R_4$ is an alkyl group such as methyl, ethyl, n-propyl, or isopropyl.

The phosphonate or phosphinate compound can includes either of the opposite stereochemical configurations [(R) or (S)], or a mixture thereof.

A method of treating leukemic cells in a mammal comprising treating the mammal with a therapeutic amount of a phosphinate having the formula:

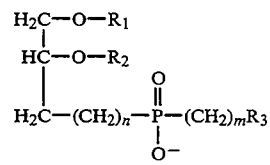

wherein $R_1$ is a long-chain alkyl group, $R_2$ is a methyl group, n=0 or 1, m=2 or 3, and $R_3$ is $N^+(CH_3)_3$, and pharmaceutically acceptable salts thereof, administered at a dosage of about 5 to 50 mg/l with or without a carrier.

The present invention also provides phospholipids with the following structures:

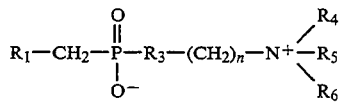

and

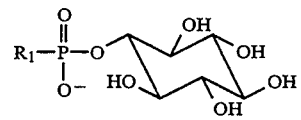

wherein $R_1$, $R_2$, $R_3$, $R_4$, $R_5$, $R_6$ and n are as defined above. The present invention provides phospholipids with an inositol group for use as anti-inflammatory agents:

wherein $R_1$ is as defined herein above.

These phosphonates and phosphinates are useful as anti-cancer agents since they inhibit growth of leukemic and tumor cells, as anti-inflammatory and anti-allergic agents, and as anti-cardiovascular agents.

The invention also involves the use of one or several of the above-mentioned phosphonates and phosphinates for treatment of cardiovascular diseases, such as septic shock (cardiogenic shock, thrombosis and others) when given at 5-50 mg/l in a pharmaceutically acceptable acid or salt thereof, and carrier.

The invention is also directed to the use of phosphonates and phosphinates in the treatment of malignant cells, solid tumors of any type, leukemia and in bone marrow transplantation.

The invention also pertains to the use of phosphonates in the treatment of inflammatory diseases of any form, for example, arthritis, inflammatory bowel diseases, colitis, and pulmonary inflammation.

Further, the invention relates to the use of phosphonates in the treatment of allergic diseases of any form, such as asthma, allergic rhenitis, hay fever, skin rashes and seasonal allergies.

DETAILED DESCRIPTION OF SPECIFIC EMBODIMENTS OF THE INVENTION

Production of the Phospholipids of the Invention (a) Synthesis of Phosphonocholines and Phosphonoglycerols The phosphonocholines and phosphonoglycerols can be synthesized according to the following reaction sequence:

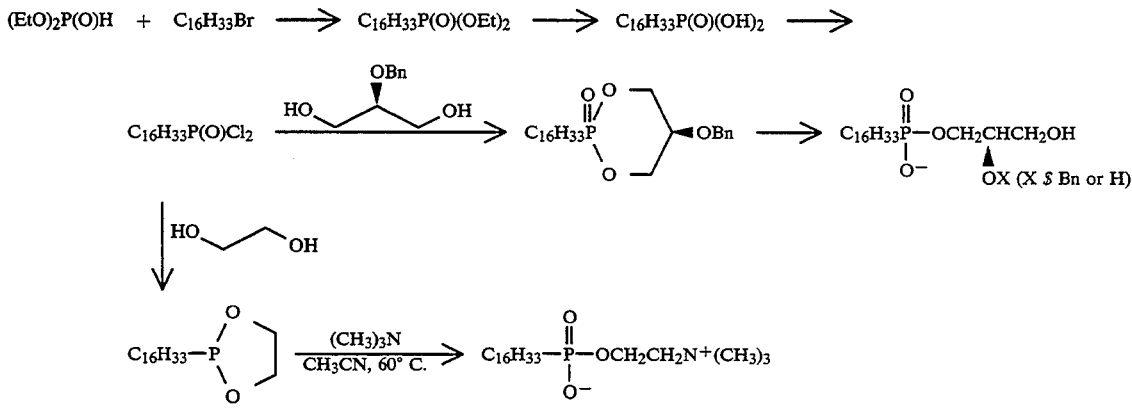

Diethyl phosphite is treated with hexadecyl (or octadecyl) bromide in a Michaelis-Becker reaction, giving the corresponding diethyl ester. The alkyl phosphonic acid is formed in situ from the ester, then treated with 2.1 equivalents of pyridine at 0° C. in tetrahydrofuran, followed by 2.1 equivalents of oxaloyl chloride at −78° C. under nitrogen. The phosphonic acid dichloride thus obtained is treated with either (R)-2-0-benzylglycerol (for conversion to phosphonoglycerol) or with ethylene glycerol to give the phospholane intermediate, which is reacted with triethylamine in acetonitrile at 75° C. in a pressure bottle to give phosphonocholine. The intermediates and products are purified by chromatography on silica gel G or by high-pressure liquid chromatography. The structures are established by nuclear magnetic resonance spectroscopy, mass spectrometry, and by elemental analysis.

(b) Synthesis of phosphonoinositol

The phosphonoinositol is prepared by the following reaction sequence:

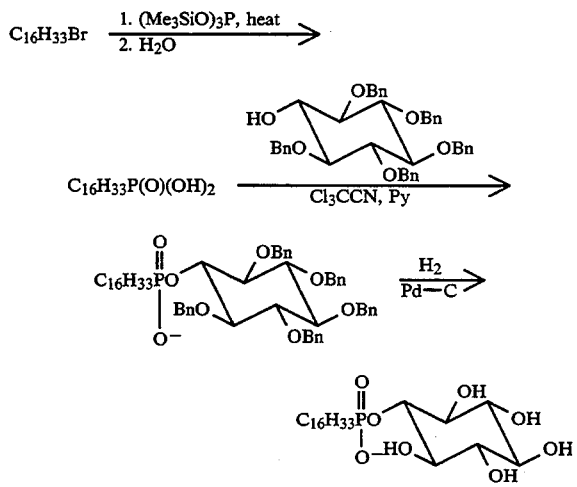

The phosphonoinositol is produced by reacting hexadecyl (or octadecyl) bromide with tris(trimethylsilyl)phosphite under argon at 135° C. to form the alkyl phosphonic acid. After the excess phosphite is removed by distillation, the residue is purified and coupled to pentabenzylinositol in the presence of trichloroacetonitrile in pyridine at 60° C. to form pentabenzylinositol phosphonate. The coupling product is purified by chromatography on silica gel, the benzyl groups are removed by catalytic hydrogenolysis, and the product phosphonoinositol is purified by cation exchange and silica gel chromatography.

(c) Synthesis of phosphonoethanolamine

The phosphonoethanolamine is prepared by the following reaction sequence:

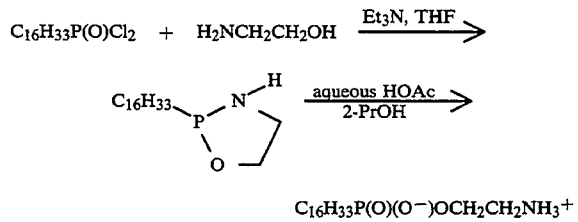

To a solution of the alkyl phosphonic acid dichloride and triethylamine in tetrahydrofuran is added a solution of 2-aminoethanol in tetrahydrofuran. Evaporation of the solvent under reduced pressure gives the intermediate phospholane, which is purified by column chromatography, dissolved in 2-propanol, and then hydrolyzed by using a mixture of glacial acetic acid in water (1:4 by volume).

(d) Synthesis of phosphonoserine

The phosphonoserine is prepared by the following reaction

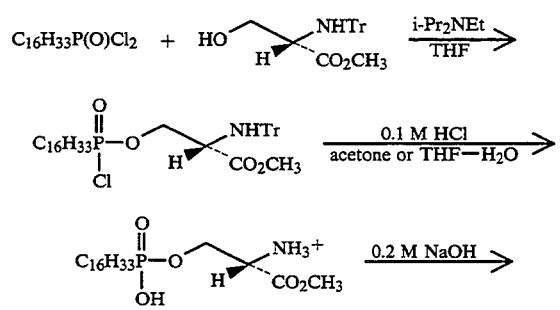

-continued

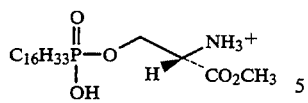

To a solution of the alkyl phosphonic acid dichloride in tetrahydrofuran and diisopropylethylamine in tetrahydrofuran is added a solution of N-tritylserine methyl ester in tetrahydrofuran. The intermediate N-tritylserine methyl ester is purified by silica gel chromatography, then subjected to detritylation with 0.1M hydrochloric acid and alkaline hydrolysis of the methyl ester. The product is purified by Dowex 50W-X8 (H+form) followed by silica gel chromatography.

(e) Production of glycerol-linked phosphonolipids

Phosphonocholines are prepared by the following reaction sequence:

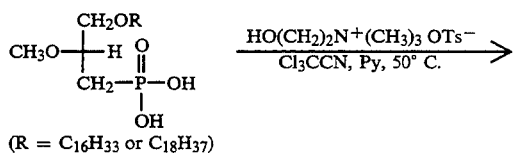

(R = $C_{16}H_{33}$ or $C_{18}H_{37}$)

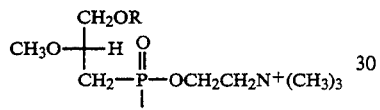

The rac-phosphonic acid shown above is prepared by proceeding according to the following sequence of reactions. First, a n-alkyl allyl ether is reacted with methanol in the presence of zinc oxide and iodine; alkyl groups other than methyl can be conveniently introduced by this method (reference: Rosenthal, A. F.; Kosolapoff, G. M.; Geyer, R. P. *Recl. Tray. Chim. Pays-Bas* 1964, 83, 1273). The 1-O-alkyl-2-O-methyliodopropane is treated with triethyl phosphite, affording the corresponding diethyl phosphonate ester, which is hydrolyzed to give the phosphonic acid. Phosphonocholine is obtained by reaction with dry choline tosylate (9 equivalents) in the presence of trichloroacetonitrile in pyridine at 50° C. for 2 days. The corresponding glycerol-linked phosphonoethanolamine is prepared by reaction of the phosphonic acid with N-(tert-butoxycarbonyl)- ethanolamine (N-t-Boc-ethanolamine) in the presence of trichloroacetonitrile or 1H-tetrazole; after purification of the coupling product by silica gel chromatography, the Boc protecting group is removed under standard conditions (50% trifluoroacetic acid in dichloromethane at 0° C.).

The corresponding glycerol-linked phosphonoserine is prepared in a similar fashion, using N-tritylserine methyl ester for coupling with the phosphonic acid. The acid-labile trityl group is removed by treatment with 0.1M hydrochloric acid in tetrahydrofuran-water (1:1), and then the methyl ester is hydrolyzed by using 0.2M sodium hydroxide. Purification is by silica gel chromatography.

(f) Production of glycerol-linked isosteric phosphonates

Isosteric phosphonates are prepared according to the following reaction sequences:

1,2,5,6-diisopropylidene-D-mannitol 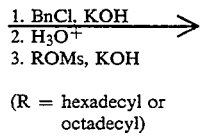

(R = hexadecyl or octadecyl)

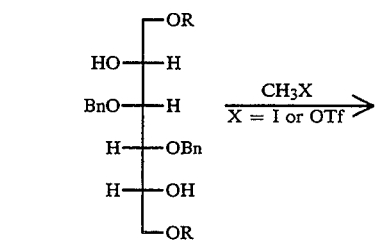

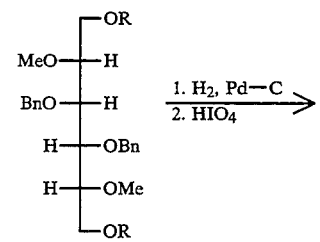

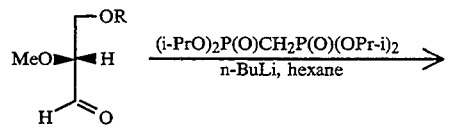

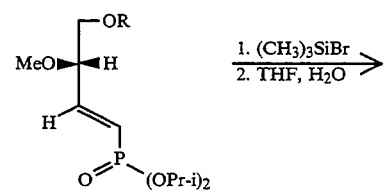

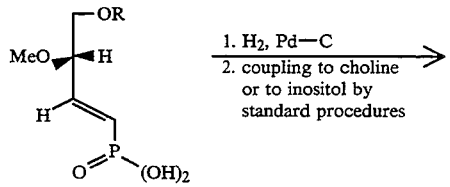

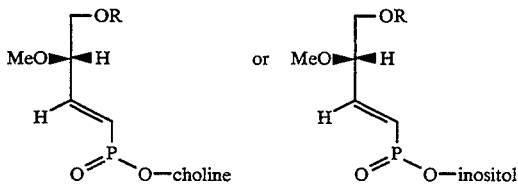

Isosteric phosphonocholine and isosteric phosphonoinositol are prepared from 1,2,5,6-diisopropylidene-D-mannitol as outlined above. First, the O-benzylation is carried out at the 3 and 4 positions, then the isopropylidene groups are removed and the primary alcohols are alkylated with long-chain alkyl groups via the mesylates or similar alkylating agents. Methylation is carried out at the 2 and 5 positions.

After catalytic hydrogenolysis, periodic acid cleavage gives the aldehyde. Reaction of the aldehyde with tetraisopropyl methylenebisphosphonate and n-butyllithium in hexane at 0° C. gives the phosphonic ester, which is hydrolyzed to the corresponding phosphonic acid by using trimethylsilyl bromide followed by aqueous workup. The vinyl group is reduced, and the phosphonic acid is coupled to choline tosylate to give the desired phosphonocholine compound or to suitably protected inositol, followed by deprotection, to give the desired phosphonoinositol compound. The products are purified by ion-exchange chromatography followed by silica gel chromatography. Phosphonoglycerols are available by a similar route.

An alternative procedure for making phosphonoinositols and phosphonocholines is illustrated below.

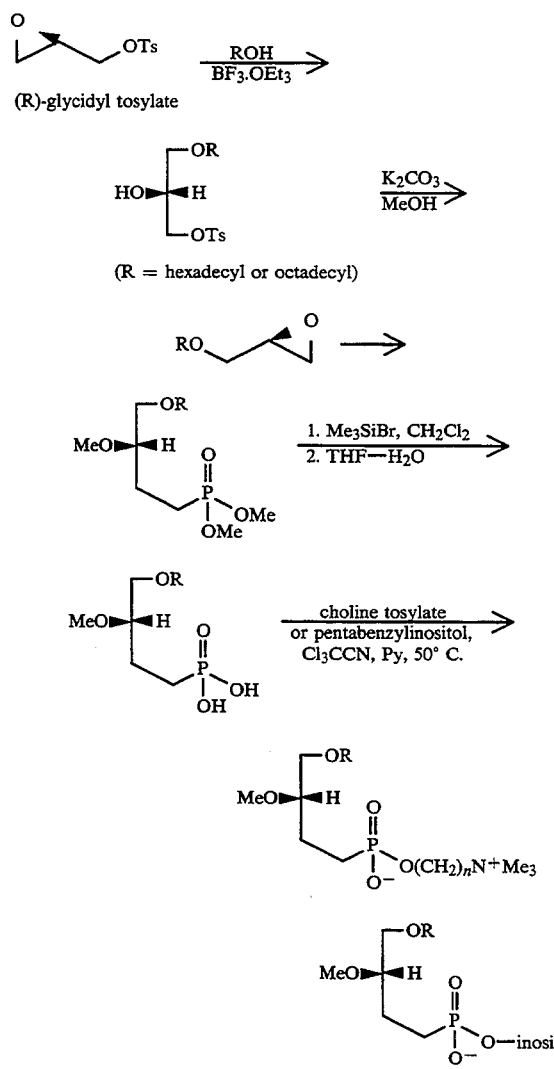

(R = hexadecyl or octadecyl)

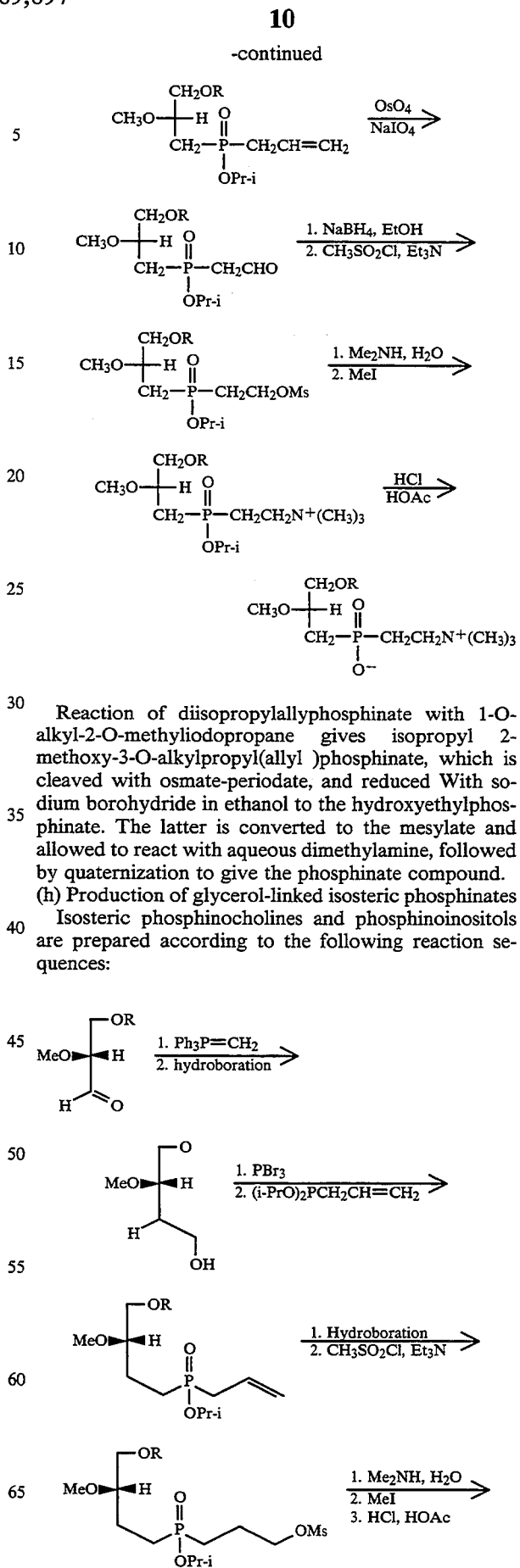

Reaction of diisopropylallyphosphinate with 1-O-alkyl-2-O-methyliodopropane gives isopropyl 2-methoxy-3-O-alkylpropyl(allyl)phosphinate, which is cleaved with osmate-periodate, and reduced With sodium borohydride in ethanol to the hydroxyethylphosphinate. The latter is converted to the mesylate and allowed to react with aqueous dimethylamine, followed by quaternization to give the phosphinate compound.

(h) Production of glycerol-linked isosteric phosphinates

Isosteric phosphinocholines and phosphinoinositols are prepared according to the following reaction sequences:

The above reaction sequence shows the use of (R)-O-hexadecyl or -octadecyl glycidol as the starting material. Use of (S)-hexadecyl or octadecyl glycidol gives the enantiomeric phosphonolipid.

(g) Production of glycerol-linked phosphinocholines

The nonisosteric phosphinocholines are prepared according to the following reaction sequence:

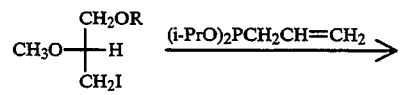

-continued

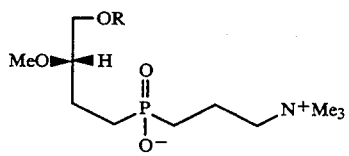

Isosteric phosphinocholine is prepared as outlined by the reaction sequence shown above. Wittig reaction of the aldehyde followed by hydroboration gives the alcohol, which is then converted into the desired phosphinate.

Hydroboration gives an alcohol (not shown) that can be coupled to a protected inositol to yield the corresponding phosphinoinositol. Mesylation of the alcohol gives the phosphinate compound, which is aminated, then treated with methyl iodide, and the phosphonate ester is hydrolyzed to give the ,isosteric phosphinocholine.

(i) Production of agents with modified distances between the phosphorus and nitrogen atoms The distance between the phosphorus and nitrogen atoms in the phosphonolipids is varied by using procedures known in the corresponding phosphate-containing compounds (references: Ali, S.; Bittman, R. *Chem. Phys. Lipids* 1989, 50, 11–21; Isaacson, Y. A.; Deroo, P. W.; Rosenthal, A. F.; Bittman, R.; Mcintyre, J. O.; Bock, H-G.; Gazzotti, P.; Fleischer, S. *J. Biot. Chem.* 1979, 254, 117–126; Ukawa, K.; Imamiya, E.; Yamamoto, H., et al. *Chem. Pharm. Bull.* 1989, 37, 1249–1255). One method for conversion of the glycerol derivative to the phosphonocholine analog with a variable number of methylene groups between the phosphorus and nitrogen atoms is shown below.

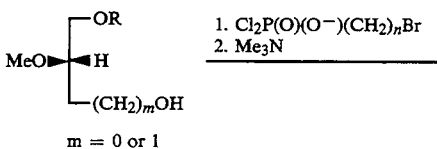

m = 0 or 1

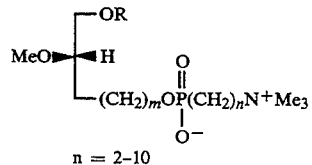

n = 2-10

Biological Activity

1. Anti-cancer activity

Several laboratory tests have been conducted to establish that phosphonates kill cancer cells.

It has been discovered that a phosphonate of the following structure:

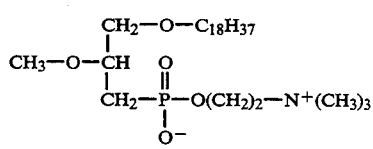

inhibits thymidine incorporation into DNA of several cancer cell lines. This behavior is indicative of anti-cancer activity.

EXAMPLE 1

Experiments were performed with three different cell lines: (1) with a mouse myelomonocytic leukemic cell line (WEHI-3B cells), (2) a human myeloleukemic cell line (HL-60 and a human cervical tumor cell line (C-41)). Cells were cultured in RPMI-1640 medium supplemented with 10% fetal bovine serum, mercaptoethanol (5 $\mu$g/ml), penicillin (50 units/ml), streptomycin (50 $\mu$g/ml), in an atmosphere of 5% $CO_2$. The cells were passaged weekly by serial 1/10 to 1/10000 dilutions. The cell viability and growth were constantly monitored by staining with trypan blue exclusion dye or the incorporation of tritiated thymidine.

$^3$H-Thymidine incorporation

Cells were placed in 96-well plates at $2 \times 10^4$ cells/well in 200 $\mu$l of medium and another 5 $\mu$l of medium containing the drugs was added. Control cultures were incubated without drugs. Cells in 96-well plates were incubated in a $CO_2$ incubator for 24 hours. The cells were then pulsed with 0.1 $\mu$Ci of [$^3$H]thymidine for 24 hours prior to the harvesting. The cells were harvested using a Brandel cell harvester model M-12, and collected on Whatman glass microfilters. The radioactivity associated with the filters was counted in a liquid scintillation counter and plotted as percent survival versus concentration of phosphonate, and the data were compared with [$^3$H]thymidine incorporation into the untreated cells.

Table 1 shows the effect of various concentrations of the phosphonate of the following formula on the growth of WEHI-3B cells:

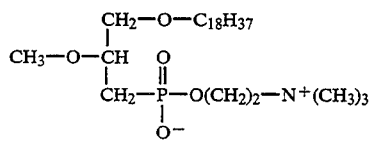

TABLE 1

| Thymidine uptake during 24 hours | |
|---|---|
| phosphate concentration ($\mu$M) | thymidine uptake (% of control) mean ± s.d. |
| 0 | 100 |
| 0.62 | 137 ± 6 |
| 1.25 | 93 ± 7 |
| 2.5 | 91 ± 4 |
| 5 | 88 ± 11 |
| 10 | 76 ± 6 |
| 20 | 48 ± 4 |
| 40 | 43 ± 15 |

Table 2 shows results of thymidine uptake by WEHI-3B and HL-60 cells during 48 hours of incubation.

TABLE 2

| Thymidine uptake during 48 hours | | |
|---|---|---|
| | thymidine uptake (% of control) | |
| phosphonate concentration ($\mu$M) | WEHI-3B cells | HL-60 cells |
| | Mean ± s.d. n = 8 | |
| 0 | 100 | 100 |
| 0.62 | 93 ± 6 | 84 ± 5 |
| 1.25 | 90 ± 5 | 76 ± 4 |
| 2.5 | 86 ± 8 | 63 ± 4 |
| 5 | 61 ± 6 | 24 ± 3 |
| 10 | 23 ± 2 | 3 ± 2 |
| 20 | 18 ± 8 | 1 ± 0 |

Table 3 shows the results of thymidine uptake by WEHI-3B and HL-60 cells during 72 hours of incubation.

TABLE 3

| | Thymidine uptake during 72 hours | |
| --- | --- | --- |
| | thymidine uptake (% of control) | |
| phosphonate concentration (μM) | WEHI-3B cells | HL-60 cells |
| | Mean ± s.d., n = 8 | |
| 0 | 100 | 100 |
| 0.62 | 85 ± 3 | 93 ± 4 |
| 1.25 | 86 ± 4 | 81 ± 4 |
| 2.5 | 82 ± 6 | 66 ± 3 |
| 5 | 60 ± 4 | 16 ± 4 |
| 10 | 26 ± 3 | 5 ± 1 |
| 20 | 10 ± 3 | 1 ± 0.9 |
| 40 | 7 ± 3 | 3 ± 1 |

Effect of phosphonate of the following structure on thymidine incorporation into DNA of WEHI-3B cells.

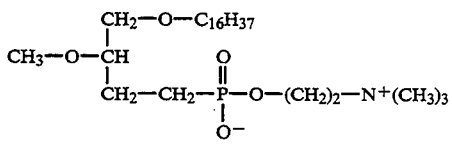

TABLE 4

| | Thymidine uptake after various days (% of control) | | |
| --- | --- | --- | --- |
| phosphonate concentration (μM) | day 1 | day 2 | day 3 |
| | | Mean, n = 5 | |
| 0 | 100 | 100 | 100 |
| 1.25 | 95 | 84 | 77 |
| 2.5 | 72 | 67 | 54 |
| 5 | 34 | 22 | 12 |
| 10 | 18 | 13 | 10 |
| 20 | 8 | 2 | 1 |
| 40 | 3 | 2 | 2 |

Table 5 demonstrates the effect of phosphonate of the above structure on the incorporation of thymidine into DNA of the C-41 cell line (a human cervical tumor cell)

TABLE 5

| Thymidine uptake into DNA of C-41 cell line | |
| --- | --- |
| phosphonate concentration (μM) | thymidine uptake (% of control) |
| | Mean, n = 3 |
| 0 | 100 |
| 2.5 | 88 |
| 5 | 63 |
| 10 | 42 |
| 20 | 41 |
| 40 | 16 |

Table 6 shows the effect of the above phosphonate on tumor growth in mice. BALB/C mice were injected with 3-Lewis lung carcinoma under the skin at the back. Three days after injection of tumor cells the treatment was initiated with 50 mg/day orally once a day. In the control group the mice received only the carrier mucilage of tragacanth. As seen in Table 6 in control animals the first sign of a detectable tumor was observed after the seventh day of post cell injection. In the phosphonate-treated animals, the tumor growth was retarded by approximately 6 days. The tumor size in the phosphonate-treated animals remained below that in the control animals throughout the experiments.

TABLE 6

| | Tumor volume (mm$^3$) | |
| --- | --- | --- |
| Days after tumor implant | control | + phosphonate |
| 0 | 0 | 0 |
| 7 | 30 | 0 |
| 10 | 120 | 0 |
| 17 | 250 | 100 |
| 18 | 432 | 175 |
| 20 | 670 | 252 |
| 22 | 810 | 500 |

2. Anti-inflammatory activity

EXAMPLE 1

Effect of the phosphonate of the following formula on the activation of human neutrophils

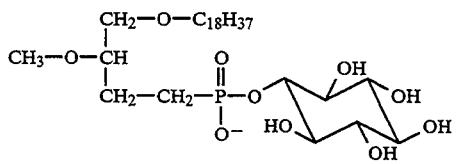

Superoxide anion generation in neutrophils has been used as an index of cell activation. The continuous spectrophotometric measurement of a superoxide dismutase inhibitable reduction of ferricytochrome C at 549 nm was used to demonstrate superoxide anion generation. Human neutrophils were stimulated with 1 μM FMLP (N-formylmethionyl-leucyl-phenylalanine). A rapid generation of superoxide was observed. Table 7 shows the inhibition of superoxide anion generation by 10 μM phosphonate after various times.

TABLE 7

| Time (min) | absorbance at 549 nm control | FMLP | FMLP + phosphonate |
| --- | --- | --- | --- |
| 0 | 0 | 0 | 0 |
| 1 | 0.001 | 0.1 | 0.03 |
| 2 | 0.002 | 0.14 | 0.04 |
| 3 | 0.01 | 0.16 | 0.04 |
| 4 | 0.015 | 0.16 | 0.04 |

EXAMPLE 2

Effect of phosphonate on neutrophil degranulation and lysosomal enzyme release (elastase)

Petri dishes were coated with [$^3$H]elastin and were used to assess the release of elastase. Neutrophils (10$^6$) in 500 μl of medium were added to each Petri dish well. Addition of 1 μM FMLP for 1 hour at 37° C. stimulated elastase release as determined by the breakdown of elastin. Phosphonate inhibited the neutrophil degranulation and the release of elastase (Table 8 ).

TABLE 8

| phosphonate concentration (μM) | μg elastin degraded/10$^6$ cells/hr |
| --- | --- |
| | Mean, n = 3 |
| 0 | 17 |
| 2.5 | 16 |
| 5 | 8 |
| 10 | 6 |
| 25 | 4 |
| 50 | 3 |

3. Anti-arthritis activity of phosphonates

In the synovial fluids of patients with arthritis there is an accumulation of two types of crystals, calcium pyrophosphate dihydrate (CPPD) and monosodium urate (MSU). These two crystals types are the major contributors to the development of arthritis by causing rapid leukocyte activation. Table 9 shows that phosphonates (50 μM) inhibited leukocyte activation in response to CPPD. Table 10 shows the inhibition in response to MSU.

TABLE 9

| Time (min) phosphonate | chemiluminescence (mV) CPPD | CPPD + |
|---|---|---|
| 0 | 0 | 0 |
| 1 | 25 | 0 |
| 2 | 175 | 0 |
| 3 | 500 | 100 |
| 4 | 750 | 275 |
| 5 | 900 | 300 |
| 6 | 800 | 250 |
| 7 | 500 | 150 |

TABLE 10

| Time (min) phosphonate | chemiluminescence (mV) MSU | MSU + |
|---|---|---|
| 0 | 0 | 0 |
| 1 | 200 | 10 |
| 2 | 500 | 50 |
| 3 | 600 | 75 |
| 4 | 675 | 80 |
| 5 | 550 | 50 |
| 6 | 400 | 20 |

4. Anti-allergic activity of phosphonates

Asthma is an allergic disease caused by the contraction of airway smooth muscles in response to activation with contractile agonists such as leukotriene $D_4$ (LTD4). As seen in Table 11, phosphonates at 5 μM inhibited LTD4-induced contraction of trachea from guinea pigs.

TABLE 11

| LTD$_4$ dose (μM) | contraction (% of max carbachol) no phosphonate | with phosphonate |
|---|---|---|
| 0 | 0 | 0 |
| 0.01 | 7 | 0 |
| 0.1 | 21 | 0 |
| 1 | 45 | 0 |
| 10 | 50 | 8 |

Inhibition of tracheal smooth muscle contraction by phosphonates supports the anti-allergic and asthmatic properties of these agents.

5. Anti-thrombolytic and cardiovascular activity

Thrombosis is the result of activation of platelets by agents such as platelet activating factor (PAF). Platelet activation is associated with aggregation and release of vasoactive compounds such as serotonin that have profound effects-on heart and vascular tissues.

The effects of phosphonate on aggregation of platelets caused by PAF or thrombin are shown in Table 12. As seen in Table 12, PAF at 1 μM or thrombin at 1 unit/ml caused 60–70% aggregation of platelets. In the presence of various concentrations of phosphonate a dose-dependent inhibition of platelet aggregation is obtained. At 10 μM of phosphonate, a complete inhibition of platelet aggregation is seen.

TABLE 12

| phosphonate dose (μM) | platelet aggregation (% of control) thrombin (1 unit) | PAF (1 μM) |
|---|---|---|
| 0 | 100 | 100 |
| 0.5 | 58 | 74 |
| 1 | 29 | 48 |
| 5 | 7.5 | 26 |
| 10 | 0 | 0 |

Phosphonates also inhibited serotonin release from platelets activated with thrombin or PAF. As seen in Table 13, phosphonate at 10 μM blocked serotonin release entirely.

TABLE 13

| phosphonate dose (mM) | serotonin release (% of control) thrombin (1 unit) | PAF (1 μM) |
|---|---|---|
| 0 | 100 | 100 |
| 1 | 76 | 80 |
| 5 | 36 | 48 |
| 10 | 16 | 28 |

The data in Table 13 support the anti-cardiovascular disease activity of phosphonates.

6. Anti-hypotensive activity

Administration of PAF intravenously causes severe hypotension. Phosphonates were shown, to block PAF-induced hypotension in rats. When given at 5 mg/kg, phosphonates inhibited the hypotensive activity of PAF dramatically. As seen in Table 14, normal rat blood pressure was about 150 mm Hg, and this dropped to about 40 mm Hg after administration of PAF (10 μg/kg). Animals given phosphonates (5 mg/kg) had only slightly reduced blood pressure after the injection of PAF, suggesting that phosphonates are anti-hypotensive agents.

TABLE 14

| PAF dose (μg/kg) | blood pressure (mm Hg) no phosphonate | with phosphonate |
|---|---|---|
| 0 | 150 | 148 |
| 0.5 | 135 | 145 |
| 1 | 120 | 145 |
| 2.5 | 100 | 140 |
| 5 | 60 | 140 |
| 10 | 40 | 130 |

These data strongly support the anti-hypotensive and cardiovascular activity of phosphonates.

Biological activity of phosphonates as anti cancer

Effects of 1-O-hexadecyl-2-O-methyl-phosphonocholine on human tumors. Two human solid tumor cell lines were evaluated for their sensitivity to the cytotoxic action of phosphonates. The soft agar colonogenic assay was used to determine the cytotoxic effect of the phosphonates. Cells were cultured in petrie dishes in methylcellulose and the number colonies formed during 5-day incubation were counted. Table 1 shows the biological activity of phosphonates on two solid tumor cells.

TABLE 15

| Drug Concentration (μM) | Cervical Carcinoma | Breast adenocarcinoma[2] Number of colonies after 5 days, mean ± S.D., n = 5 % of controls |
|---|---|---|
| 0 | 100 | 100 |
| 1.25 | 97 ± 8 | 102 ± 10 |
| 2.5 | 87 ± 7 | 89 ± 11 |
| 5 | 71 ± 8 | 84 ± 6 |

TABLE 15-continued

| Drug Concentration (μM) | Cervical Carcinoma | Breast adenocarcinoma[2] |
|---|---|---|
| | Number of colonies after 5 days, mean ± S.D., n = 5 % of controls | |
| 10 | 52 ± 6 | 68 ± 5 |
| 20 | 31 ± 4 | 47 ± 6 |
| 40 | 12 ± 2 | 16 ± 3 |

[1]C41 cell line, derived from human with cervical carcinoma
[2]MCF-7 cell line, derived from human with breast adenocarcinoma Biological activity of phosphonates against leukemia and lymphoma was also studies. We used DHL4 (a human B cell lymphoma), HeL (a human erythroid leukemia), JRT3T3, Jurkett ( a human T-cell lymphoma), and KG1 α(a human myeloid leukemia). Using soft agar colonogenic assay as an index of cell growth the effectiveness of 1-O-alkyl-2-O-methyl-glycerophosphonocholine was investigated. Table 16 shows the cytotoxic activity of the phosphonates.

TABLE 16

| Phosphonate concentration (μM) | DHL4 | HeL | JRT3T3 | KG1α |
|---|---|---|---|---|
| | Colonies formed after 5-days (% of control) Mean ± S.D., n = 5 | | | |
| 0 | 100 | 100 | 100 | 100 |
| 1.25 | 76 ± 7 | 91 ± 8 | 87 ± 6 | 78 ± 8 |
| 2.5 | 61 ± 5 | 72 ± 5 | 65 ± 7 | 56 ± 6 |
| 5 | 42 ± 6 | 58 ± 4 | 34 ± 5 | 41 ± 4 |
| 10 | 18 ± 4 | 26 ± 5 | 20 ± 3 | 15 ± 3 |
| 20 | 5 ± 1 | 12 ± 3 | 8 ± 2 | 7 ± 1 |
| 40 | 0 | 1 ± 0.5 | 3 ± 1 | 4 ± 1 |

As table 16 shows phosphonates are also highly affective in preventing growth of both leukemia and lymphoma cells.

In addition to human cancerous cell lines, phosphonates showed to be highly effective in preventing mouse derived cancer cell lines. Among the cell types that we studies three cell lines grow as solid tumors and one grows in the lymphatic system. These included Lewis Lung carcinoma (LLC), L1210, P388 and WEHI-3B cell lines. Lewis lung carcinoma is a cancer cell line derived from lung of mice with tumor. P388 is a macrophage lineage grow under the skin and produces tumor. L1210 is a mouse lymphoma cell line which is derived from lymph nodes in mice. WEHI-3B cells are myelomonocytic lineage that grow as solid tumor and metastasize in the lung, blood, spleen and various other organs. Table shows the effect of phosphonates on the formation of colonies by these cells using soft agar assay technique.

TABLE 17

| Phosphonate concentration (μM) | LLC | P388 | L1210 | WEHI-3B |
|---|---|---|---|---|
| | Colonies formed after 5-days (% of non-treated cells). Mean, n = 5 | | | |
| 0 | 100 | 100 | 100 | 100 |
| 1.25 | 97 ± 9 | 88 ± 6 | 91 ± 7 | 88 ± 6 |
| 2.5 | 81 ± 6 | 79 ± 8 | 80 ± 11 | 50 ± 6 |
| 5 | 67 ± 5 | 61 ± 7 | 55 ± 4 | 48 ± 5 |
| 10 | 53 ± 4 | 56 ± 7 | 42 ± 5 | 34 ± 4 |
| 20 | 37 ± 5 | 29 ± 4 | 22 ± 3 | 13 ± 3 |
| 40 | 19 ± 6 | 16 ± 2 | 14 ± 5 | 2 ± 1 |

Phosphonates also showed to be highly effective in vivo in retarding tumor growth in mice. Table 18 shows that treatment of mice with 25 mg/kg per day given phosphonate intramuscularly reduced the tumor growth significantly. WEHI-3B were grown under the skin in BALB/C mice at $1 \times 10^6$ cells per mice. After 3 days one group (n=5) of mice received daily 500 μg of phosphonate intramuscularly. The tumor size was measured using a calliper. Table 18 shows the tumor size in phosphonate treated and untreated mice.

TABLE 18

| Days after implantation | Tumor volume in cm³ (mean ± s.d.), n = 5 | |
|---|---|---|
| | Controls (no drug treated) | animals treated with drug |
| 3 | 0.009 ± 0.001 | 0.000 ± 0.000 |
| 15 | 0.024 ± 0.004 | 0.000 ± 0.000 |
| 17 | 0.138 ± 0.062 | 0.000 ± 0.000 |
| 20 | 0.219 ± 0.089 | 0.036 ± 0.010 |
| 22 | 0.705 ± 0.234 | 0.117 ± 0.017 |
| 24 | 0.952 ± 0.111 | 0.172 ± 0.025 |

The table 18 clearly demonstrates that phosphonates are potent anti-cancer agents effective in vivo.

We have also studied the effect of phosphonates on a mouse model of lymphoma. Mice (CD1) were injected with $1 \times 10^6$ L1210 (B-cell lymphoma) intraperitonealy. In one group the mice received phosphonate (1-O-hexadecyl)-2-O-methyl-glycero-3phosphonocholine at 10 mg/kg per day intramuscularly. The control animals (untreated animals) started to die usually after 7 days of cancer cell injection, as the lymph nodes and marrows grew extensive number of cancer cells. None of the drug treated animals died up to 21 days of observation. Table 19 shows the percentage of animals died after the initiation of lymphoma.

TABLE 19

| Days after drug treatment | Untreated (controls) | Drug treated |
|---|---|---|
| | % survival | |
| 0 | 100 | 100 |
| 7 | 83 | 100 |
| 8 | 50 | 100 |
| 19 | 33 | 100 |
| 21 | 0 | 100 |

The results clearly demonstrated that, phosphonates were highly effective in preventing death due to lymphoma.

It is concluded that, phosphonates are effective anti-cancer drugs that can reduce mortality caused either by solid tumors such as, breast cancer, cervical cancer, lung cancer and skin cancer, or leukemia and lymphoma.

The Following Work Was Carried Out With C-4-Phosphastes of the Following Structures

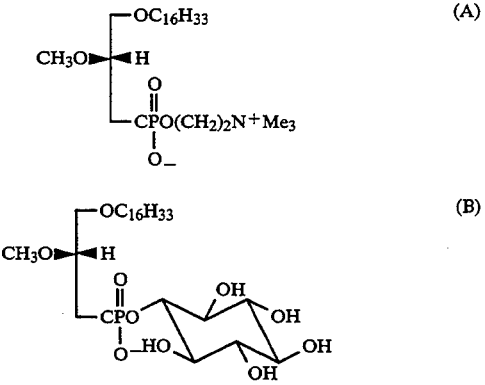

The experiments presented in this communication are performed with both compounds A and B, but due to the availability of larger amount of compound A, in hand, most of the in vivo experiments were carried out with compound (A). The results provided are the mean of at least three determinations.

"Phosphonates as antiinflammatory agents"

1—Effects of phosphonates on superoxide anion generation in human neutrophils. Phosphonates inhibit phospholipase C dependent activation of human neutrophils. Inflammatory reactions are caused predominantly by the activation of neutrophils in response to various inflammatory mediators. One of the most important activator of human neutrophil is a peptide of the derivative of bacterial toxin, known as formyl-methionyl-leucyl-phenylalanine (FMLP). The effects of FMLP (1 $\mu$M) on the generation of superoxide anion from human neutrophils in response to FMLP was investigated. The continuous spectrophotometric measurement of a superoxide dismutase inhibitable reduction of ferricytochrome C at 549 nm was measured. In the presence of 500 units of catalase and 1.24 mg/ml of cytochrome C in buffer. The release of $O_2-$ in the presence and absence of phosphonate (A) are shown in table 20.

TABLE 20

| Phosphonate concentration ($\mu$M) | Absorbance at 549 nm (after 3 min) |
|---|---|
| 0 | 0.189 |
| 0.5 | 0.175 |
| 1 | 0.125 |
| 5 | 0.09 |
| 10 | 0.04 |
| 25 | 0.0 |

These results suggest that phosphonates block the tissue damages caused by the release of oxygen radicals, thus supporting our claim, phosphonates as antiinflammatory agents.

2—Effects of phosphonates against neutrophils degranulation and elastase release. Further to support our claim that phosphonates are antiinflammatory agents, the effects of phosphonate (A) on the degranulation and release of lysosomal enzymes in neutrophils were studied. Neutrophil degranulation and the release of lysozomal enzymes such as elastase is one of the most contributing factor to the development of inflammatory reactions. We have investigated the effects of phosphonate (A) on the release of elastase by neutrophils. Human neutrophils were stimulated with 1 $\mu$M FMLP and the generation of elastase was measured using a radioenzymoassay technique. Table 21 shows inhibition of elastae release from neutrophils by various concentrations of phosphonate.

TABLE 21

| Phosphonate concentrations ($\mu$M) | Elastin degraded ($\mu$g/$10^6$ cells) |
|---|---|
| 0 | 18 |
| 0.5 | 17 |
| 1 | 17 |
| 5 | 9 |
| 10 | 6 |
| 25 | 3 |
| 50 | 0 | these results clearly supports the antiinflammatory role of phosphonates.

3—Phosphonates as anti-arthritis In the synovial fluids of patients with arthritis there has been the accumulation of two types of crystals, calcium pyrophosphate dehydrate (CPPD), and monosodium urate (MSU). These two types are known to be the major contributor to the causation of arthritis, particularly the gout.

Table 22 shows the effect of phosphonate (A) on chemiluminescence induced in human platelets in response to activation with CPPD crystals.

TABLE 22

| | Chemiluminescence (mV) | |
|---|---|---|
| Time (min) | no phosphonate | + phosphonate |
| 0 | 0 | 0 |
| 1 | 25 | 0 |
| 2 | 175 | 0 |
| 3 | 500 | 100 |
| 4 | 750 | 275 |
| 5 | 900 | 300 |
| 6 | 800 | 250 |
| 7 | 500 | 150 |

These results demonstrated that phosphonates at 25 $\mu$M effectively inhibited CPPD crystals induced human blood neutrophils activation.

Effects of MSU crystals on the activation of human neutrophils and its inhibition by phosphonates (50 $\mu$M) is shown in table 22

TABLE 23

| | Chemiluminescence (mV) | |
|---|---|---|
| Time (min) | no phosphonate | + phosphonate |
| 0 | 0 | 0 |
| 1 | 200 | 10 |
| 2 | 500 | 50 |
| 3 | 600 | 75 |
| 4 | 675 | 80 |
| 5 | 550 | 50 |
| 6 | 400 | 20 |

Results of table 22 and 23 suggest that phosphonates are effective in the treatment of arthritis and other inflammatory reactions that CPPD crystals and MSU crystals are playing major roles.

"Phosphonates as anti-asthma drugs"

Effect of phosphonates on the inhibition of tracheal contraction. (LTD4) is one of the most important mediator of human asthma. LTD4 causes contraction of airway smooth muscles leading to severe bronchoconstriction. The action of phosphonate (B) at 5 $\mu$M on LTD4 induced contraction of trachea is investigated. As can be seen from the table 24 phosphonate (B) at 5 $\mu$M effectively inhibited contraction caused by LTD4. Phosphonate (A) was about a log dose less active in inhibiting LTD4 induced tracheal contraction.

TABLE 24

| LTD4 dose ($\mu$M) | contraction (% of max carbachol) | |
|---|---|---|
| | no phosphonate | + phosphonate |
| 0 | 0 | 0 |
| 0.01 | 7 | 0 |
| 0.1 | 21 | 0 |
| 1 | 45 | 0 |
| 10 | 50 | 8 |

The data demonstrated that phosphonates effectively block agonist induced contraction of airway smooth muscles. Contraction of airway smooth muscles is the main feature of human asthma. Thus the data support the claim that phosphonates can be used as anti-asthma drugs.

The principal action of phosphonates in biological system is the inhibition of phospholipase C an essential enzyme in the transmission of signals to the cells by variety of inflammatory, and vasoactive mediators.

Table 25 supports the claim that phosphonates are inhibitors of phospholipase C in biological system.

Activation of phospholipase C lead to the hydrolysis of phospholipids containing the sugar inositol. These phospholipids known as phosphatidylinositol, phosphatidylinositol monophosphate and phosphatidylinositol bisphosphate. Thus activation of phospholipase C leads to the hydrolysis of above the phospholipids and the resultant is the formation of inositol phosphates and diacylglycerol. We therefore investigated the hydrolysis of phosphatidylinositol in smooth muscle cells by activation with LTD4 and carbachol. The formation of inositol phosphates such as inositol trisphosphate (IP3), inositol bisphosphate (IP2), and inositol monophosphates (IP1) were measured. Phosphonate (A) also effectively inhibited the formation of IP3, IP2, and IP1 in airway smooth muscles in response to the activation with LTD4 and carbachol.

TABLE 25

| phosphonate B concentration ($\mu$M) | IP1 | IP2 | IP3 |
| --- | --- | --- | --- |
| 0 | 100 | 234 | 148 |
| 1 | 100 | 190 | 260 |
| 10 | 83 | 170 | 178 |
| 100 | 76 | 142 | 177 |

Table 26 shows inhibition of inositol phosphates formation by AlF4 and GTP$\gamma$S stimulated smooth muscle cells.

TABLE 26

| Phosphonate (B) concentration ($\mu$M) | IP1 | IP2 | IP3 |
| --- | --- | --- | --- |
| 0 | 240 | 1142 | 338 |
| 1 | 148 | 1090 | 343 |
| 10 | 126 | 956 | 332 |
| 100 | 95 | 116 | 102 |

These data clearly demonstrate that the site of action of phosphonates is the phospholipase C.

Phosphonates toxicity

In vivo tests in rats. Phosphonate (A) given i.v. to the rats up to 10 mg/kg did not have any effects on the normal respiratory function. The expiration or inspiration in rats remained unaffected. At 10 mg/kg phosphonate (A) slightly (10-20%) reduced blood pressure, but this was short lived and after the withdrawal of the drug, the blood pressure returned to normal. Given phosphonates orally at the 10 mg/kg did not reduce blood pressure significantly, suggesting the p.o. route should be a better route for the administration of the drug. Administration of phosphonates i.v. or p.o did not produce nerve toxicity as the sciatic nerve reflexes was normal up to concentrations greater than 10 mg/kg. Administration of phosphonates i.v. or p.o. did not affect the normal heart function ( the EKG parameters remained normal). If phosphonates were given i.v,. at concentrations of about 10 mg/kg a reduction in blood pressure was seen, but this was short lived and as soon as the drug was removed the blood pressure returned to normal. However if phosphonates were given orally up to 50 mg/kg no reduction in blood pressure was seen.

Effects of phosphonates in human. In one trial by one of the inventors (HS) phosphonate (A) was taken twice a day ( 10 mg) orally. No sign of discomfort, pain, or stomach upset was noticed. In fact there was no changes in the normal behavior and body activity due to phosphonates absorption.

Treatment of human inflammatory reactions by phosphonates.

Phosphonate (A) was used to treat inflammation of human wrist. Two days treatment of human inflamed wrist with the cream of phosphonates significantly reduced the level of swelling and pain. Once again there was no sign of any side effects or muscle stiffness. These preliminary results indicate that phosphonates are effective in reduction of pain and edema in human inflammation without visible side effects.

Summary

The C-4-phosphonates such as compounds A and B are inhibitors of Pi-phospholipase C (PLC) with compound B being the most active. Both class of phosphonates inhibit physiological responses that are initiated through the activity of PLC. Phosphonates inhibit neutrophils, platelets and smooth muscle activation in response to variety of agonists. Phosphonates are effective in vivo with minimal of side effects. Phosphonates are highly useful as anti-inflammation, anti-thrombosis, and anti-asthma.

Usage and Dosage

An effective concentration of phosphonate (normally 5-50 mg/l) can be given orally, intravenously (i.v.), intramuscularly (i.m.) or subcutaneously (s.c.), in the form of tablets (orally), capsules (orally), or injection arepules (i.v., i.m., s.c.). The drug can be applied in the form of a rubbing cream. Tablets can be prepared via compression of 50 mg of phosphonates, 200 mg of lactose, and 50 mg Avicel(TM). Capsules are made by making bilayers of liposomal phosphonates in the concentrations of 5-50 mg with lecithin Injection solutions are made either in water or propylene glycol with an upwardly adjusted pH in phosphate buffer. The drug solution is sterilized through a filter of 0.22 min. Solutions can be made in 20% propylene glycol with about 0.5% of a preservative such as ascorbic acid.

As will be apparent to those skilled in the art in the light of the foregoing disclosure, many alterations and modifications are possible in the practice of this invention without departing from the spirit or scope thereof.

What is claimed is:

1. A method of treating lymphoma, lung carcinoma or leukemia in a mammal afflicted with lymphoma, lung carcinoma or leukemia comprising treating the afflicted mammal with a therapeutic amount of a compound of the formula:

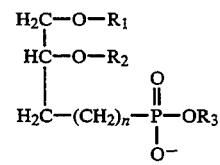

wherein n is 0 or 1 and $R_1$ is an alkyl group of $C_{16}$ or $C_{18}$; wherein $R_2$ is a methyl group; and wherein $R_3$ is a $(CH_2)_m N^+(CH_3)_3$ group with m=2.

2. A method as claimed in claim 1 wherein $R_1$ is an alkyl group of 18 carbon atoms and n=0, used in the treatment of lung carcinoma.

3. A method of treating lymphoma or leukemia, in a mammal afflicted with lymphoma or leukemia, the method comprising treating the mammal with a therapeutic amount of a compound of the formula:
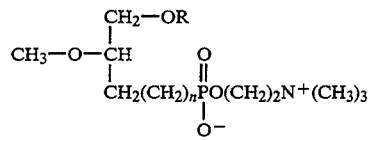
wherein R is a hexadecyl alkyl group and n=0, or the enantiomer thereof, or a mixture of stereoisomers.
4. A method as claimed in 1 or 3 wherein the phosphonate compound includes either of the opposite stereochemical configurations [(R) or (S)] or a mixture thereof.
* * * * *